United States Patent [19]

Silfverskiold

[11] Patent Number: 4,790,301
[45] Date of Patent: Dec. 13, 1988

[54] DEVICE FOR AND METHOD OF DYNAMIC SPLINTING

[76] Inventor: Krister Silfverskiold, Mellangatan 25, 413 01 Gothenburg, Sweden

[21] Appl. No.: 113,213

[22] Filed: Oct. 23, 1987

[51] Int. Cl.[4] ............................. A61F 5/04; A61F 5/10
[52] U.S. Cl. ....................................... 128/87 A; 128/77
[58] Field of Search .................... 128/85, 87 A, 77; 47/67; 368/141, 142, 143, 144; 242/84.3, 107.4

[56] References Cited

U.S. PATENT DOCUMENTS

| | | | |
|---|---|---|---|
| 174,031 | 2/1876 | Thornton | 368/141 |
| 1,964,998 | 7/1934 | Perrine | 242/84.3 |
| 2,175,756 | 10/1939 | Maury | 242/84.3 |
| 3,506,214 | 4/1970 | Laszlo | 242/84.3 |
| 3,621,650 | 11/1971 | Schnyder et al. | 368/144 |
| 4,187,996 | 2/1980 | Ehrlich | 47/67 |
| 4,216,922 | 8/1980 | Weman | 242/107.4 |
| 4,328,794 | 5/1982 | Holmes | 128/85 |
| 4,346,857 | 8/1982 | Moll | 242/84.3 |
| 4,363,553 | 12/1982 | Thomi et al. | 368/142 |
| 4,556,184 | 12/1985 | O'Sullivan | 47/67 |
| 4,623,113 | 11/1986 | Studebaker | 47/67 |
| 4,644,938 | 2/1987 | Yates et al. | 128/77 |

*Primary Examiner*—Robert A. Hafer
*Assistant Examiner*—Michael Brown
*Attorney, Agent, or Firm*—Edwin D. Schindler

[57] ABSTRACT

A system of dynamic hand splinting employing a splinting device which comprises a line attached between a finger to be treated and a rotatable spool acted upon by a watch spring which via the spool and line transmits to the finger a force appropriate for assisting straightening or bending movements of the finger.

8 Claims, 5 Drawing Sheets

DEVICE FOR AND METHOD OF DYNAMIC SPLINTING

FIELD OF THE INVENTION

This invention relates to a device for dynamic splinting and to a method of dynamic splinting, more especially dynamic hand splinting.

BACKGROUND TO THE INVENTION

In connection with hand injuries or after an operation a patient is sometimes treated by hand therapy which involves dynamic hand splinting, which is a treatment for assisting, stabilising or re-establishing movements of one or more fingers by facilitating specific finger movements via the action of a spring mechanism acting on the finger.

Dynamic hand splinting is commonly used in connection with:

nerve injuries, to prevent muscle imbalance and maintain a passive range of motion during rehabilitation;

arthroplastie in finger joints, to assist extension or flexion while maintaining a correct plane of motion;

tendon injuries, to assist movements without the use of the injured tendon; and contractures, to supply a stretching force across finger joints.

PRIOR ART

Currently, most dynamic hand splinting techniques employ different arrangements of rubber bands to supply the necessary force. Other current techniques employ coil springs or spring wire as power sources.

Rubber band techniques are subject to a variety of disadvantages of which inconvenience to the patient must be considered of primary importance. For optimal function with as constant force as possible, the rubber band is commonly attached to the base of a splint along the patient's forearm.

This is a vulnerable position prone to catching on external objects, hindering the patient in various activities, most notably dressing and undressing. Breakage is a frequent problem. Pulleys are often used to lower the profile of the splint, and in this context the rubber band is commonly connected to a line running over or under the pulley before connecting to the patient's finger, but these arrangements do not shorten the length of rubber bands extending along the forearm. Other disadvantages are loss of elasticity with use, and difficulty in measuring the force applied.

Coil springs avoid some of the problems of rubber band techniques but are just as inconvenient for the patient as they also extend along the forearm, as they likewise usually connect to a line passing around a pulley before connecting to the finger. In the alternative, spring wire used as a flexible outrigger extending from the splint, while avoiding the use of a line and pulley, is bulky and cumbersome due to its bow shape extending over the hand and has not achieved popularity.

It is an object of this invention to provide an improved method of dynamic splinting and device for practicing said method wherein in the field of dynamic hand splinting the disadvantages of the above-described known techniques are at least substantially reduced or avoided.

It is a further object of the invention to provide a novel splinting method and device, more especially but not exclusively hand splinting, having improved patient convenience, improved reliability, improved reproducibility of the applied force and the possibility of achieving a more uniform force over the entire range of movement permitted, simplified attachment to the patient and easier adjustment of the force applied to suit a particular patient's requirements.

THE INVENTION

According to one aspect of the present invention, there is provided a device for effecting dynamic hand splinting comprising:

a first part for attachment to one part of the limb of the patient;

a second part for attachment to a second part of the limb of the patient, which second limb part is jointed to the first limb part;

a spring mechanism interconnecting said first and second parts of the device, said spring mechanism comprising:

a rotatable spool;

a line which is windable on to and off the spool and has a portion leading away from the spool which is attached to said second device part;

a support carrying said spool and attached to said first device part; and at least one spring acting with torsion on the spool to urge said spool in the rotational sense in which the line is wound up thereon.

A preferred spring is a torsion spring having properties analogous to the properties of springs used in mechanical watches, and therefore for convenience referred to hereinafter as a watch spring.

According to another aspect of the invention, there is provided a method of dynamic splinting according to which movement of part of the limb of a patient is improved or assisted by application to said limb part of a force derived from a spring which acts with torsion on a spool on which a line can be wound by rotation of the spool, said spring acting to wind the line on to the spool and the line having a portion leading away from the spool which is attached to the limb part to enable or improve movement of said limb part by winding or unwinding the line on the spool.

The invention is especially suitable for dynamic hand splinting, in which the first part of the device is attached to at least one of the forearm and/or hand of the patient and the second part is attached to one or more fingers.

In an embodiment of the device to be described, the support is constituted by a cylindrical housing accommodating the spool and the watch spring, and said housing carries means for attaching said housing to said first device part. Conveniently, said cylindrical housing fixedly carries on its axis means defining an axis of rotation for the spool, the watch spring is accommodated in a spring barrel mounted to the spool for rotation therewith, and the watch spring is connected between said axis-defining means and said spring barrel. The spring housing preferably comprises two cylindrical parts each open at one end and which fit together at their open ends in a plane normal to the axis of said housing, said two cylindrical housing parts being relatively rotatable to adjust the tension of the watch spring.

The said first device part may take various constructions according to the type of injury sustained and/or treatment and exercise required. The following examples refer to the situation where the invention is applied to dynamic hand splinting, to enable or assist movement of a finger.

Often, in this situation, said first device part will comprise a splint for application to at least the region of the hand adjacent the finger, a substantially rigid outrigger having substantially parallel arms is mounted to said splint and the spool support is formed with mounting means adapted for mounting said spool support to the outrigger between the free ends of the parallel arms thereof. It is a further preferred feature of the invention that said outrigger is mounted to said splint by means of a mounting plate and at least one fixing screw engaged into punched holes in said splint, avoiding the usual requirement for heat bonding or rivetting.

For assisting extension of the finger, for example, the splint may extend along the back of the forearm partway up the back of the hand, an outrigger extending therefrom to a point above the back of the finger to enable the spring mechanism to be connected between a finger cuff and the free end of the outrigger. An alternative splint, employed to assist flexing of a finger when the tendon has been repaired, may be shaped to extend in a curve fully over the back of the hand to the end of the fingers, and having an associated band extending across the palm to which a specially shaped outrigger is attached to enable the spring mechanism to be connected between a point above the palm and a finger cuff applied to the tip of the finger. In this alternative splint, the curved portion extending behind the fingers may sometimes not be required.

The invention also extends to the case where said first device part is attached to the hand with a soft wrap and the spool support is formed with mounting means adapted for mounting said spool support to a safety pin pinned to the soft hand wrap.

As previously mentioned, the spool and watch spring may be accommodated within a housing which is mounted to a substantially rigid outrigger itself mounted to a rigid splint applied to at least the hand of the patient. Alternatively, the housing is mounted by means of a safety pin to a soft wrap applied around at least part of the palm of the hand.

It will be understood that, for exercising two or more fingers, separate spring mechanisms, one for each finger, may be employed, each connecting between a common hand splint or hand wrap and a finger cuff or finger pad applied to the respective finger.

BRIEF DESCRIPTION OF DRAWINGS

The method of and device for hand splinting in accordance with the invention are exemplified with reference to the accompanying drawings, in which.

DESCRIPTION OF EMBODIMENTS

Figure 1:
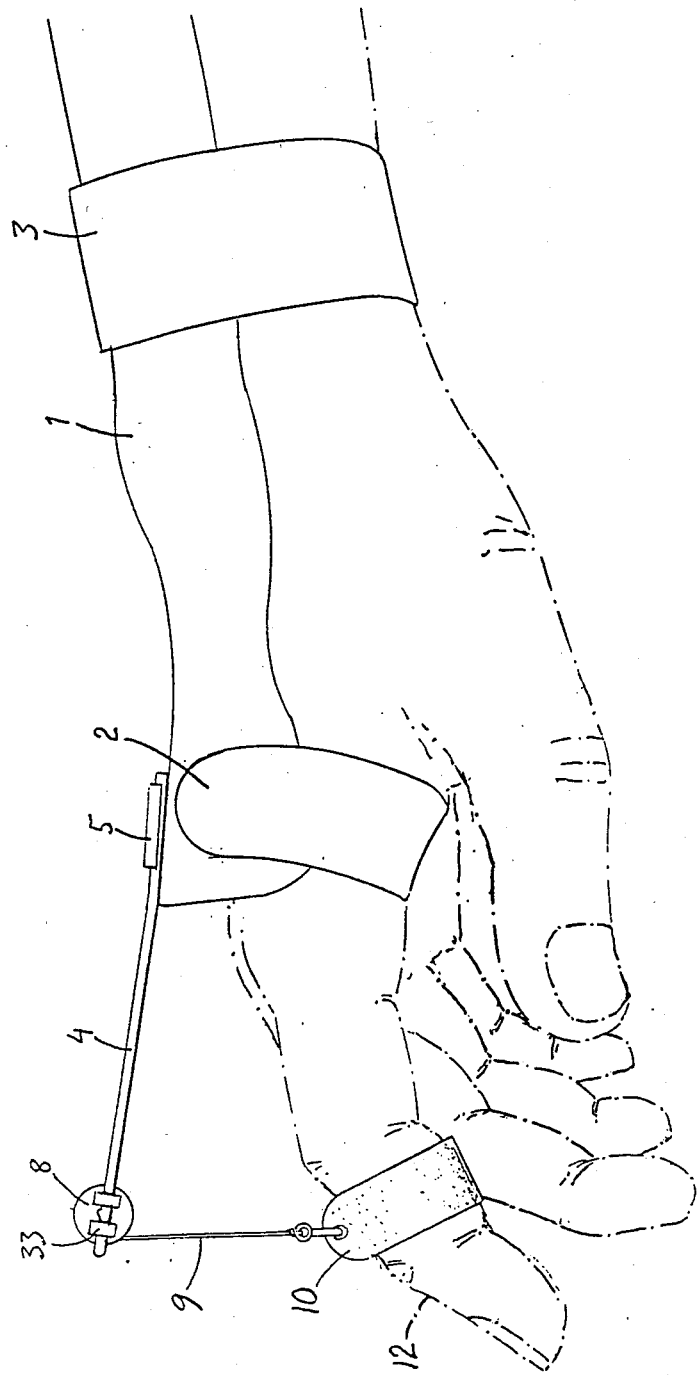
FIG. 1 shows a first embodiment of a dynamic hand splint in side view.
Figure 2:
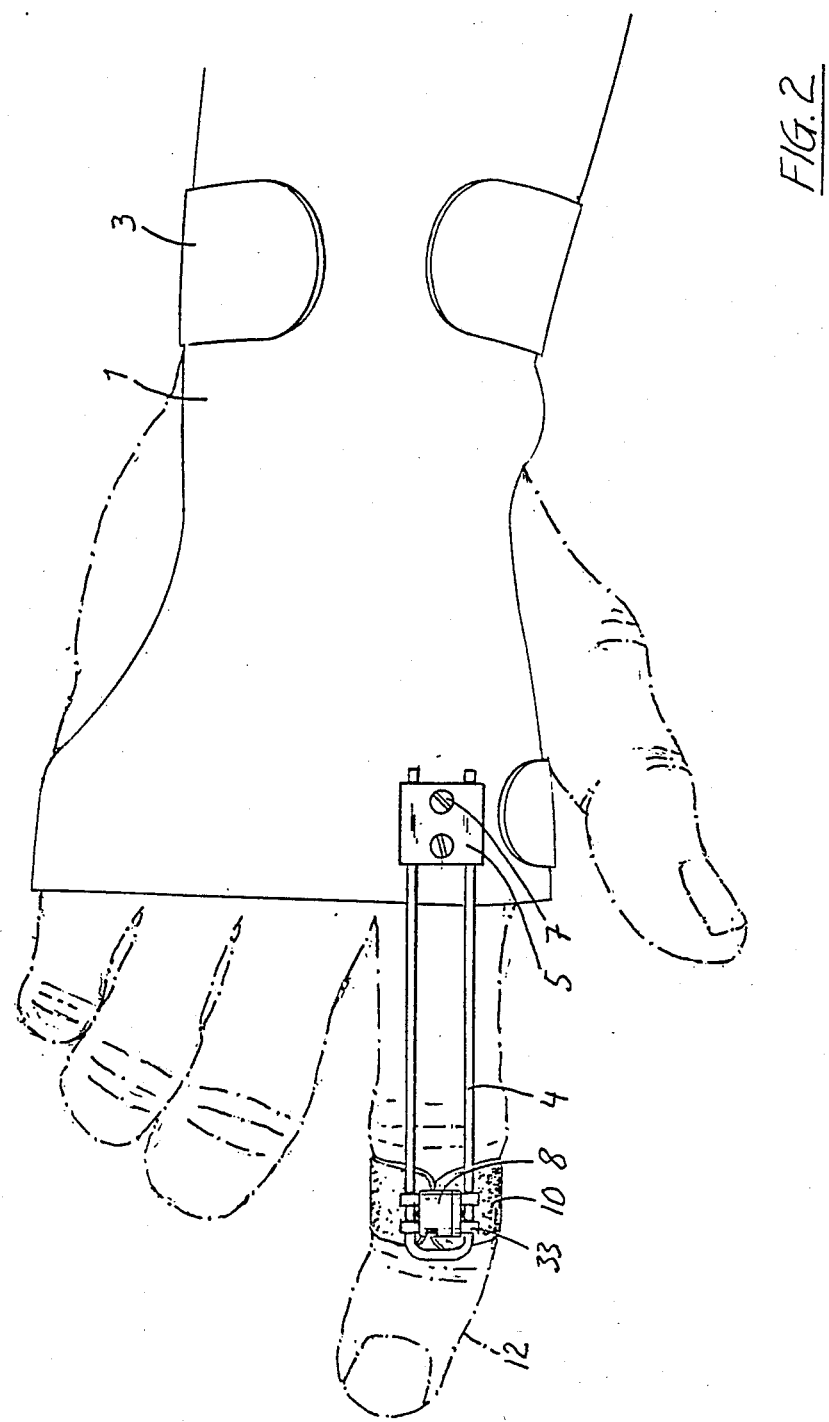
FIG. 2 shows the splint from above.

According to the embodiment of FIGS. 1 and 2, the splint consists of a first part 1 in the form of a rigid splint, preferably of plastics material, which fits over the back of the hand and forearm. It is fastened in position with two straps 2 and 3.

At the front end of the splint adjacent the fingers a U-shaped outrigger 4 is attached to said splint by means of a fastening plate 5 secured to the splint with fastening screws 7 engaged into punched holes in the splint.

The outrigger 4 has generally parallel arms connected by a crosspiece at its outer or free end remote from the splint, and is fixed in position to extend along and above the back of a finger to be treated.

At the outer end of the outrigger 4 is mounted a spring mechanism 8 to be later described. From the spring mechanism 8 a line 9 extends to the finger 12 to be treated, in order to subject said finger to the force of the spring mechanism. The line 9 is attached to the finger via a ring secured to a finger cuff 10. The force of the spring mechanism 8 which is transmitted through the line 9 thus acts to extend or straighten the finger 12.

Figure 3:
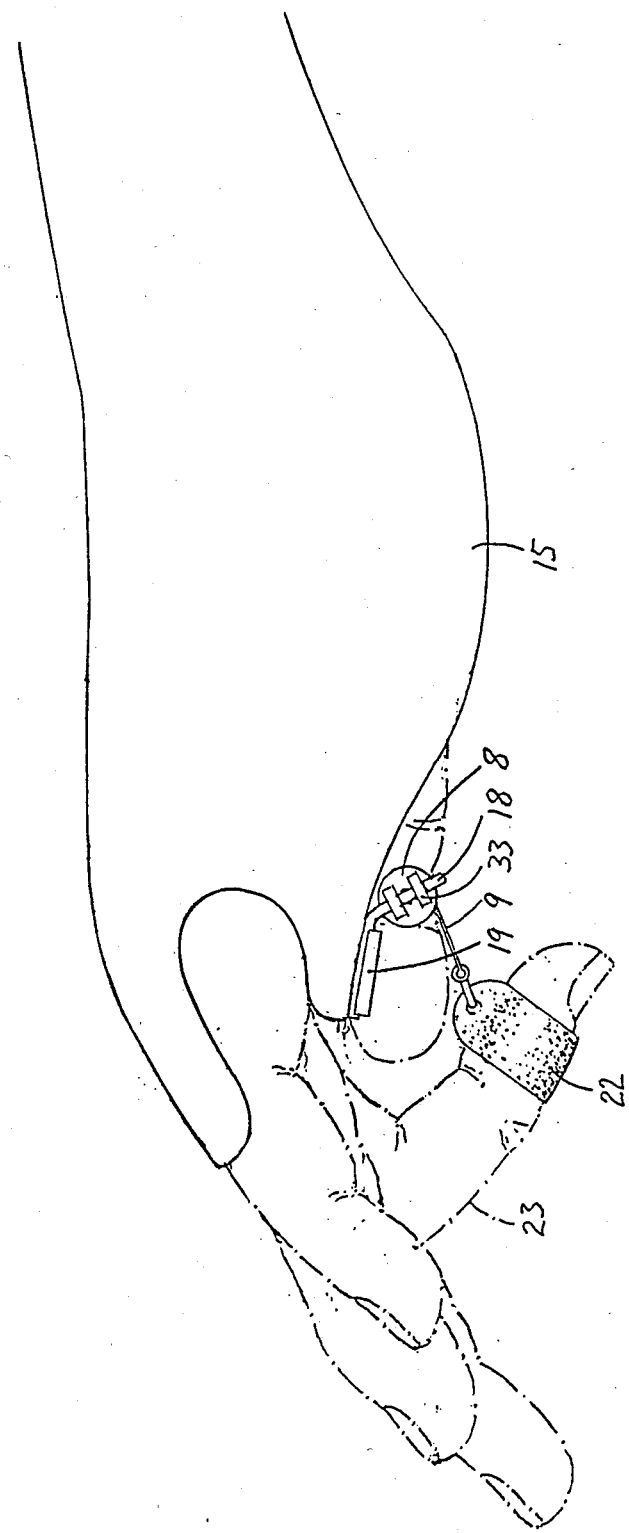
FIG. 3 shows a second embodiment in side view.

The embodiment of the splint shown in FIG. 3 also consists of a rigid splint 15 shaped to fit around the hand and forearm. A U-shaped but shorter and angled outrigger 18 is attached to the splint with a fastening plate 19 and fastening screws, as described with reference to FIGS. 1 and 2.

The outrigger carries a spring mechanism 8 of the construction to be later described. The spring mechanism 8 is connected to a ring and finger cuff 22 through a line 9, the finger cuff being applied to the finger 23 to be treated.

In this case it is presumed that the flexor tendon of the finger is injured or that the flexion capacity is diminished due to stiffness. The force of the spring mechanism 8 thus acts through the line 9 to flex or bend the finger.

Figure 4:
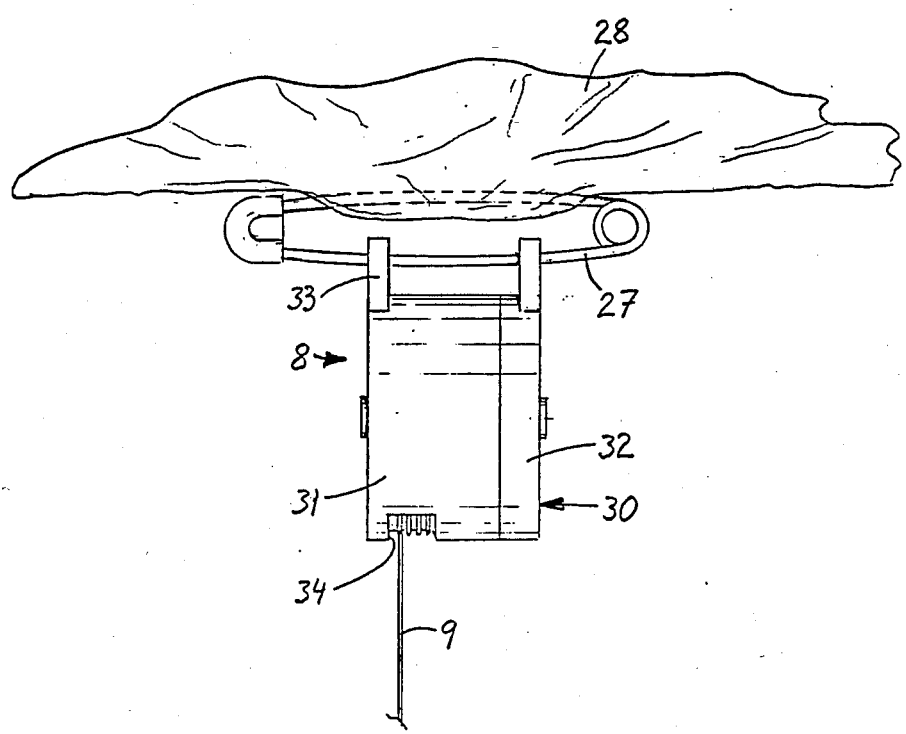
FIG. 4 is a partial view of a third embodiment.

In the latter case when the spring force acts to flex or bend a finger, a circumferential splint can be substituted for a dorsal splint. Such a splint can then be held to the hand and arm with a plastics band or with a soft wrap such as a crepe bandage. A spring mechanism can then be positioned adjacent the palm of the hand, in a similar position to that shown in FIG. 3, by pinning it to the bandage. Such an embodiment is shown in FIG. 4. A safety pin 27 is connected to the spring mechanism 8 and pinned to the bandage 28. This type of splint is again suitable for a treatment in which the principal requirement is to assist flexing of the finger. When using the splint to extend or straighten a finger (FIGS. 1 and 2), the position required for the spring mechanism over the finger will not usually allow its attachment to a soft bandage.

Figure 5:
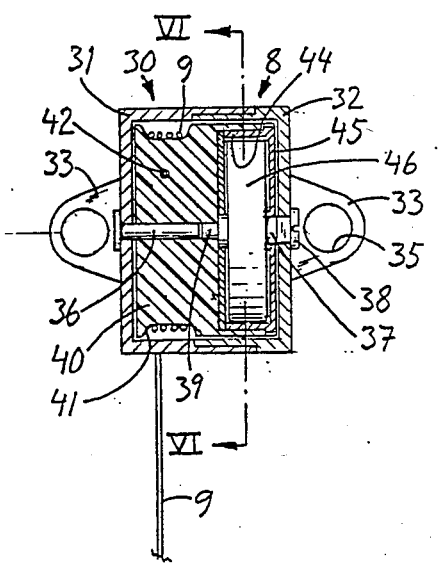
FIG. 5 shows a spring mechanism in cross-section on the line 5—5 in FIG. 6.
Figure 6:
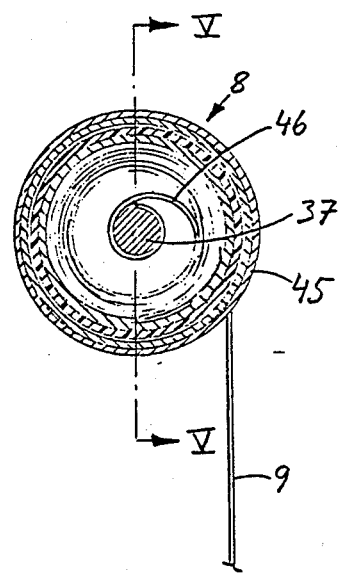
FIG. 6 shows the spring mechanism in cross-section on the line 6—6 in FIG. 5.

The spring mechanism is shown in FIGS. 5 and 6. It consists of a housing 30 made of two cylindrical parts 31 and 32. These housing parts may be fabricated of metal or of plastics material. The side aspect of each part has two aligned apertured brackets 33 (see FIGS. 1 and 3), each with an aperture 35. The brackets enable the arms of the outrigger 4 to be passed through the apertures 35, thus mounting the housing 31, 32 to said outrigger. In the case shown in FIG. 4 where a safety pin 27 is used, the brackets 33 extend externally of the housing 30 in planes parallel to the housing side walls and, in this instance, only two such brackets are necessary. These modified brackets can alternatively be made as openable rings, thus facilitating attachment to the arms of the safety pin.

It is alternatively possible, in the embodiment of FIGS. 1 and 3 where the spring mechanism 8 attaches to an outrigger 4, to provide the cylindrical wall of the housing 31, 32 with bracket means in the form of one or more spring hooks which mount to the cross-piece of the U-shaped outrigger instead of to the parallel side arms thereof.

The two cylindrical parts 31 and 32 are each closed at one end only to overlap at their open ends and thus mutually guide each other into position when fitted together. They are held together in the fitted condition by friction, a snapping mechanism or adhesive.

From the side of part 31, an axle 36 extends to the inside of the housing 30. To the side of part 32, an axle 37 with a reduced diameter extension 39 is attached with a screw 38. The axle 37 is locked to the housing part 32 by a square end which fits into a square hole in the side of part 32. The axle parts 36, 37 and 39 can alternatively be made as one part, each end connected to housing parts 31 and 32 with a screw, which also serves to hold the two housing parts 31 and 32 together.

A line spool 40 for winding the line 9 is mounted on aligned axle 36 and axle extension 39. The line 9 is attached by knotting to the spool 40 either through a hole in the spool side or wall or, as shown in FIG. 5, in the spool body 42. Part 31 of the housing 30 has an opening 34 (see FIG. 4) throgh which the line 9 emerges from the spool.

The spool 40 carries a cylindrical cup 44 housing a spring barrel 45. The barrel 45 can be opened and contains a watch spring 46. The inner end of the spring is attached to the axle 37 and the outer end is attached to the barrel 45. The spring 46 is thus mounted so that it will wind itself up on axle 37 when the line 9 is pulled out from the spool 40, the outer end of the spring rotating with the spool 40 and the barrel 45, while the inner end of the spring remains fixed in position with the axle 37 and the housing 30. It is possible for the spool 40 and the spring barrel 45 to be made as a single integral part.

When a splint shown in FIGS. 1 and 2 is used, the pull of the line 9 extending from the spring mechanism 8 will produce a force acting to extend the finger to which the finger cuff 10 is attached. In this example, it is assumed that the extensor tendon is damaged and the splint serves to assist the extension of the finger. The undamaged flexor tendon will work against the force of the spring mechanism when flexing the finger.

As the finger flexes the line 9 will be pulled out. The spool 40 will turn around the axle 36 and the spring 46 winds up on the axle 37 which connects the inner end of the spring to the housing 30. The spring barrel 45 rotates with the spool 40, together with the outer end of the spring 46. The housing 30 is in turn immobilized by its attachment to the outrigger 4, which is achieved by the mounting of the bracket means 33 to the outrigger arms.

On extension of the finger, the line 9 will wind up on the spool 40 as the spring 46 acts to turn the spring barrel 45. The spring mechanism functions in the same way in the embodiments of the splint shown in FIGS. 3 and 4. The spring mechanism 8 is in these embodiments attached either to the outrigger 18 or to the safety pin 27. As mentioned above, in this case the spring mechanism acts to flex the finger and take the tension off the flexor tendon.

The shape of the spring mechanism is very advantageous. For the required forces it can be made very small. Its cylindrical shape and immobile casing minimises the risk of catching on external objects and lessens the inconvenience of the splint for the patient. The encasement of the mechanism and its rounded, smooth shape are thus important characteristics.

The spring mechanism can be manufactured to generate different forces by incorporating different size springs and each such individual unit can be adjusted within its working range by winding the spring to different tensions. This is easily effected by turning one part of the housing relative to the other, with the line fully wound up on the spool.

A watch spring is a well proved device which, even with the small dimensions required for this invention, can be made with a low spring constant. It should also be mentioned that a watch spring can be modified to give a substantial even force over its entire working range. In a known method for achieving this, the spring acts on a cone shaped spool, thus giving it a variable moment arm. Alternatively, the mechanism may be designed with a double spring wound between two axles, the spring winding in opposite directions on the two axles.

Modifications such as these are included within the spirit and scope of the present invention as hereinbefore described.

In addition, the device is also easy to attach to the patient. The above-described outrigger construction is simple and can, with the aid of the above-described plate and screws, readily be attached to the splint. The outrigger is easily cut to a suitable length and/or bent to enable appropriate positioning of the spring mechanism.

The device in accordance with the invention may be provided as a kit ready for assembly as a dynamic splint, the spring mechanism being either ready mounted or ready for mounting to the outrigger by the bracket means. However, while several embodiments of practical splints have been hitherto described, the method of dynamic splinting in accordance with the invention can alternatively be practised in various constructions of splints wherein a line is attached between the finger or other part of a limb to be exercised or movement assisted and a rotatable spool acted upon with torsion by a force derived from a watch or equivalent spring.

What is claimed is:

1. A dynamic splinting device, comprising:
   a first device part for attachment to one part of a limb of a patient;
   a second device part for attachment to a second part of the limb of the patient, said second part of the limb of the patient being a different part than the part of the limb of the patient to which said first device part is attached to, the second limb part of the patient being jointed to the first limb part of the patient; and,
   a spring mechanism serving as a means for providing a force for the dynamic splinting and movement of a digit of the patient, said spring mechanism being the sole means for interconnecting said first device part and said second device part, said spring mechanism comprising:
   a rotatable spool;
   a line which is windable on to and off of the spool and has a portion leading away from the spool which is attached to said second device part;
   a support carrying said spool and attached to said first device part; and
   at least one spring acting with torsion on the spool to urge said spool in the rotational sense in which the line is wound up thereon.

2. A device according to claim 1, wherein said spring is a torsion spring.

3. A device according to claim 2, wherein said support is constituted by a cylindrical housing accommodating the spool and the torsion spring, and said housing carries means for attaching said housing to said first part.

4. A device according to claim 3, wherein said cylindrical housing fixedly carries on its axis means defining an axis of rotation for the spool, the torsion spring is accommodated in a spring barrel mounted to the spool for rotation therewith, and the torsion spring is connected between said axis-defining means and said spring barrel.

5. A device according to claim 4, wherein the cylindrical housing comprises two cylindrical parts each open at one end and which fit together at their open ends in a plane normal to the axis of said housing, said two cylindrical housing parts being relatively rotatable to adjust the tension of the torsion spring.

6. A device according to claim 1, intended for dynamic hand splinting, wherein said first device part comprises a splint for application to at least the region of the hand adjacent a finger, a substantially rigid outrigger having substantially parallel arms is mounted to said splint and the spool support is formed with mounting means adapted for mounting said spool support to the outrigger between the free ends of the parallel arms thereof.

7. A device according to claim 6, wherein said outrigger is mounted to said splint by means of a mounting plate and at least one fixing screw engaged into punched holes in said splint.

8. A device according to claim 7, wherein said first device part includes a soft hand wrap for at least the palm of the hand and the spool support is formed with mounting means adapted for mounting said spool support to a safety pin pinned to the soft hand wrap.

* * * * *